(12) United States Patent
Ok et al.

(10) Patent No.: US 11,738,123 B2
(45) Date of Patent: Aug. 29, 2023

(54) IMPLANT HAVING CONTROLLED GENERATION RATE OF REACTIVE OXYGEN SPECIES AND METHOD OF CONTROLLING GENERATION OF REACTIVE OXYGEN SPECIES USING THE SAME

(71) Applicants: KOREA INSTITUTE OF SCIENCE AND TECHNOLOGY, Seoul (KR); KOREA UNIVERSITY RESEARCH AND BUSINESS FOUNDATION, Seoul (KR)

(72) Inventors: Myoung-Ryul Ok, Seoul (KR); Jimin Park, Seoul (KR); Yu Chan Kim, Seoul (KR); Hyun Kwang Seok, Seoul (KR); Hyung-Seop Han, Seoul (KR); Hojeong Jeon, Seoul (KR); Hyunseon Seo, Seoul (KR); Jee-Wook Lee, Seoul (KR); Jin Kyung Jeon, Seoul (KR); Gayoung Jung, Seoul (KR); Jong Woong Park, Seoul (KR); Ji Hun Park, Seoul (KR)

(73) Assignees: Korea Institute of Science and Technology, Seoul (KR); Korea University Research and Business Foundation, Seoul (KR)

( * ) Notice: Subject to any disclaimer, the term of this patent is extended or adjusted under 35 U.S.C. 154(b) by 418 days.

(21) Appl. No.: 16/891,195

(22) Filed: Jun. 3, 2020

(65) Prior Publication Data

US 2020/0384165 A1 Dec. 10, 2020

(30) Foreign Application Priority Data

Jun. 5, 2019 (KR) .......................... 10-2019-0066915
Nov. 20, 2019 (KR) .......................... 10-2019-0149796

(51) Int. Cl.
*A61L 31/16* (2006.01)
*A61B 17/86* (2006.01)
(Continued)

(52) U.S. Cl.
CPC .............. *A61L 31/16* (2013.01); *A61B 17/80* (2013.01); *A61B 17/8605* (2013.01);
(Continued)

(58) Field of Classification Search
CPC ....... A61L 31/16; A61L 31/022; A61B 17/80; A61B 17/8605; A61B 17/866;
(Continued)

(56) References Cited

U.S. PATENT DOCUMENTS

| 6,168,633 B1 * | 1/2001 | Shoher | ................. | A61L 27/306 433/173 |
| 8,114,148 B2 * | 2/2012 | Atanasoska | ........... | A61L 31/022 623/1.15 |

(Continued)

FOREIGN PATENT DOCUMENTS

| KR | 1020110114993 A | 10/2011 |
| KR | 1020130034288 A | 4/2013 |

(Continued)

*Primary Examiner* — Kevin T Truong
*Assistant Examiner* — Diana Jones
(74) *Attorney, Agent, or Firm* — Rabin & Berdo, P.C.

(57) ABSTRACT

Provided is an implant having a controlled generation rate of reactive oxygen species and a method of controlling generation of reactive oxygen species using the same. The implant having a controlled generation rate of reactive oxygen species according to the present invention includes a body formed of a metallic material and having a groove, a first filling metal filling one region of the groove, and a second filling metal filling the groove on the first filling metal, wherein the second filling metal has an ionization tendency different from that of the first filling metal.

37 Claims, 6 Drawing Sheets

(51) Int. Cl.
  *A61B 17/80* (2006.01)
  *A61K 9/00* (2006.01)
  *A61K 33/00* (2006.01)
  *A61L 31/02* (2006.01)
  *F16B 35/04* (2006.01)
  *A61F 2/28* (2006.01)
  *A61B 17/00* (2006.01)
  *C25D 11/00* (2006.01)

(52) U.S. Cl.
  CPC .......... *A61B 17/866* (2013.01); *A61F 2/2846* (2013.01); *A61K 9/0024* (2013.01); *A61K 33/00* (2013.01); *A61L 31/022* (2013.01); *F16B 35/04* (2013.01); *A61B 2017/00893* (2013.01); *C25D 11/00* (2013.01)

(58) Field of Classification Search
  CPC ........ A61B 2017/00893; A61F 2/2846; A61K 9/0024; A61K 33/00; F16B 35/04; C25D 11/00
  See application file for complete search history.

(56) References Cited

U.S. PATENT DOCUMENTS

| | | |
|---|---|---|
| 2004/0230225 A1 | 11/2004 | Penner et al. |
| 2009/0326638 A1* | 12/2009 | Atanasoska ........... A61L 31/148 623/1.38 |
| 2011/0015756 A1* | 1/2011 | Pawar ................... A61L 27/306 427/2.26 |

FOREIGN PATENT DOCUMENTS

| | | |
|---|---|---|
| KR | 101878853 B1 | 7/2018 |
| KR | 1020180080173 A | 7/2018 |
| KR | 1020200140111 A | 12/2020 |

* cited by examiner

1 step : FIRST METAL LAYER(Zn insert)

FIG. 3B

2 step : SECOND METAL LAYER(Mg insert)

FIG. 4A 1 step : SINGLE METAL LAYER(Zn insert)

FIG. 4B 2 step : SINGLE METAL LAYER(Zn insert)

IMPLANT HAVING CONTROLLED GENERATION RATE OF REACTIVE OXYGEN SPECIES AND METHOD OF CONTROLLING GENERATION OF REACTIVE OXYGEN SPECIES USING THE SAME

CROSS-REFERENCE TO RELATED APPLICATION

This application claims the benefit of Korean Patent Application No. 10-2019-0066915, filed on Jun. 5, 2019, and Korean Patent Application No. 10-2019-0149796, filed on Nov. 20, 2019, respectively, in the Korean Intellectual Property Office, the disclosures of which are incorporated herein in their entirety by reference.

BACKGROUND

1. Field

The present invention relates to an implant having a controlled generation rate of reactive oxygen species and a method of controlling generation of reactive oxygen species using the same, and more particularly, to an implant having a controlled generation rate of reactive oxygen species such that a generation rate of reactive oxygen species is high at an early stage and decreases over time and a method of controlling generation of reactive oxygen species with time using the same.

2. Description of the Related Art

Extensive research into various physiological mechanisms of reactive oxygen species (ROS) has revealed an effect of the reactive oxygen species on promoting angiogenesis. In addition, reactive oxygen species have immune function capable of preventing infection of injury by bacteria or virus. However, reactive oxygen species are chemically unstable, and thus generation of excessive reactive oxygen species may cause problems such as damage to normal cell membranes and cells.

Meanwhile, during or after a dental implant procedure, sites of surgery may be infected by bacteria or the like due to environmental properties of oral cavity. Such infection may cause osteomyelitis, periodontal disease, gum inflammation, and the like. Thus, at an early stage of the procedure, infection at the surgery site can be prevented by introducing reactive oxygen species having antimicrobial defense properties into the treatment site. However, as the risk of infection caused by surgery decreases, excessive reactive oxygen species is disadvantageous in tissue regeneration, and thus the concentration of reactive oxygen species need to be maintained at the low level enough for angiogenesis but not dangerous to tissues. In addition, during the fracture healing process, supplementation of low dose reactive oxygen species at the fracture site in the early stage of hematoma formation can promote neoangiogenesis, resulting in shortening total healing time of fracture.

Techniques for generating reactive oxygen species at an implant procedure site require an external instrument such as light source for photocatalytic generation or electric power supply for electrochemical generation of reactive oxygen species or use instrument-free electrochemical oxygen reduction reaction (ORR) based on the ionization tendency difference between different metals.

SUMMARY

According to such conventional techniques of generating reactive oxygen species, it is impossible to appropriately control the generation rate of reactive oxygen species in accordance with the bone healing process over time after the internal fixation with an implant insertion.

The present invention has been proposed to solve various problems including the above problems, and an object of the present invention is to provide an implant capable of realizing both antimicrobial defense properties in accordance with a procedure site of the implant and angiogenic function by controlling the generation rate of reactive oxygen species, and a method of manufacturing the same. However, these problems to be solved are illustrative and the scope of the present invention is not limited thereby.

Additional aspects will be set forth in part in the description which follows and, in part, will be apparent from the description, or may be learned by practice of the presented embodiments.

According to an aspect of the present invention to achieve the object, provided is an implant having a controlled generation rate of reactive oxygen species including: a body formed of a metallic material and having a groove; a first filling metal filling a region of the groove; and a second filling metal filling the groove on the first filling metal, wherein the second filling metal has an ionization tendency different from that of the first filling metal, and both the first filling metal and the second filling metal have ionization tendencies higher than that of the body.

The second filling metal may have a higher ionization tendency than that of the first filling metal.

One of the first filling metal and the second filling metal may be zinc (Zn) or a Zn alloy, and the other may be magnesium (Mg) or a Mg alloy.

One of the first filling metal and the second filling metal may be iron (Fe) or a Fe alloy, and the other may be Zn, a Zn alloy, Mg, or a Mg alloy.

One of the first filling metal and the second filling metal may be a pure metal, and the other may be an alloy including the pure metal as a main metal.

The first filling metal and the second filling metal may be alloys including the same main metal and having different composition ratios.

The body may include one selected from titanium (Ti), a Ti alloy, stainless steel, and a cobalt-chromium (Co—Cr) alloy.

According to another aspect of the present invention, provided is an implant having a controlled generation rate of reactive oxygen species including: a body formed of a metallic material and having a groove; and a filling metal filling at least one region inside the groove, wherein the groove includes an upper region having a cross-sectional area different from a cross-sectional area of a lower region, the filling metal fills at least one portion of the upper region having the different cross-sectional area, and the filling metal has a higher ionization tendency than that of the body.

The cross-sectional area of the lower region may be smaller than the cross-sectional area of the upper region.

The groove may include a portion in which a cross-section increases in a tapered shape from the lower region to the upper region.

The filling metal may be zinc (Zn), a Zn alloy, magnesium (Mg), or a Mg alloy.

The body may be formed of titanium (Ti), a Ti alloy, stainless steel, or a cobalt-chromium (Co—Cr) alloy.

The groove may have a shape extending vertically downward from a top surface of the body with a predetermined depth.

According to another aspect of the present invention, provided is a method of controlling a generation rate of reactive oxygen species using an implant including a first filling metal and a second filling metal both having higher ionization tendencies than that of a body, the method including: a first step of generating reactive oxygen species by ionization of the second filling metal caused by galvanic corrosion between the second filling metal and the body; and a second step of generating reactive oxygen species in a concentration different from a concentration of reactive oxygen species obtained in the first step by ionization of the first filling metal caused by galvanic corrosion between the first filling metal and the body after the first step, and the first filling metal and the second filling metal have different ionization tendencies.

The ionization tendency of the second filling metal may be higher than that of the first filling metal, and the concentration of reactive oxygen species generated in the second step may be lower than the concentration of reactive oxygen species generated in the first step.

According to another aspect of the present invention, provided is a method of controlling a generation rate of reactive oxygen species using an implant having a groove formed to have different cross-sectional areas and filled with a filling metal having a higher ionization tendency than that of a body, the method including: a first step of generating reactive oxygen species by ionization of the filling metal having a first cross-sectional area; and a second step of generating reactive oxygen species in a concentration different from the concentration of reactive oxygen species obtained in the first step by ionization of the filling metal having a second cross-sectional area different from the first cross-sectional area after the first step.

The concentration of reactive oxygen species generated in the second step may be lower than the concentration of reactive oxygen species generated in the first step.

According to another aspect of the present invention, provided is a method of manufacturing an implant having a controlling generation rate of reactive oxygen species, the method including: preparing a body having a groove; filling one region inside the groove with a first filling metal; and filling another region on the first filling metal with a second filling metal, wherein the second filling metal has an ionization tendency different from an ionization tendency of the first filling metal.

The second filling metal may have a higher ionization tendency than that of the first filling metal.

The fillings with the first and second filling metals may be performed by directly inserting the first and second filling metals into the groove.

The fillings with the first and second filling metals may include: injecting a molten fluid of the first filling metal into the groove and solidifying the molten fluid; and injecting a molten fluid of the second filling metal onto the first filling metal and solidifying the molten fluid.

The fillings with the first and second filling metals may include: inserting a powder of the first filling powder to the groove and sintering the powder; and inserting a powder of the second filling metal onto the first filling metal and sintering the powder.

The fillings with the first and second filling metals may include: sequentially inserting powders of the first filling metal and the second filling metal to the groove and sintering the powders.

According to another aspect of the present invention, provided is a method of manufacturing an implant having a controlled generation rate of reactive oxygen species, the method including: preparing a body having a groove; and filling at least one region of the groove with a filling metal, wherein the groove includes an upper region having a larger cross-sectional area than a cross-sectional area of a lower region, and the filling of the groove with the filling metal includes filling the groove with the filling metal up to a portion of the upper region.

The filling of the groove with the filling metal may be performed by directly inserting the filling metal into the groove.

The filling of the groove with the filling metal may include injecting a molten fluid of the filling metal into the groove and solidify the molten fluid.

The filling of the groove with the filling metal may include injecting a powder of the filling metal to the groove and sintering the powder.

According to another aspect of the present invention, provided is an implant having a controlled generation rate of reactive oxygen species including: a body formed in a shape corresponding to an implant hole of a bone fixation plate having a plurality of implant holes formed at intervals through which fixation implants configured to fix a fracture part of the broken bone are inserted, and inserted into a position corresponding to the fracture site of the bone among the implant holes; and a first filling metal filling a recessed portion recessed from one surface of the body, wherein the first filling metal has an ionization tendency higher than an ionization tendency of a metal constituting the body.

The body may be formed of one metallic material selected from titanium (Ti), a Ti alloy, stainless steel, and a cobalt-chromium (Co—Cr) alloy.

The first filling metal may be zinc (Zn), a Zn alloy, magnesium (Mg), or an Mg alloy.

A second filling metal having a higher ionization tendency than that of the first filling metal may fill the recessed portion on the first filling metal.

The first filling metal may be zinc (Zn) or a Zn alloy, and the second filling metal may be magnesium (Mg) or a Mg alloy.

The first filling metal may be iron (Fe) or a Fe alloy, and the second filling metal may be Zn, a Zn alloy, Mg, or a Mg alloy.

The recessed portion may include an upper region having a larger cross-sectional area than a cross-sectional area of a lower region, and the first filling metal fills at least one portion of the upper region having the larger cross-sectional area than that of the lower region.

According to another aspect of the present invention, provided is a fracture fixation device including: a bone fixation plate disposed on at least one portion of a broken bone and having a plurality of implant holes formed at intervals; a first fixing implant penetrating one of the plurality of implant holes of the fixation plate to be inserted into a first fracture part of the bone to fix the first fracture part; a second fixing implant penetrating another implant hole of the fixation plate to be inserted into a second fracture part of the bone to fix the second fracture part; and a functional implant engaged into another implant hole of the fixation plate at a position corresponding to the fracture site of the bone, generating reactive oxygen species, and supplying the reactive oxygen species to the fracture site.

The functional implant does not include a threaded portion extending downward from a head portion and inserted into at least one portion of the bone.

According to another embodiment, the fixation plate may be formed of a metallic material.

According to another embodiment, the fixation plate and the functional implant may be in electrical contact with each other.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Hereinafter, embodiments of the present invention will be described in detail with reference to the accompanying drawings.

The invention may, however, be embodied in many different forms and should not be construed as being limited to the embodiments set forth herein. Rather, these embodiments are provided so that this disclosure will be thorough and complete, and will fully convey the concept of the invention to those skilled in the art. In the drawings, the thicknesses of layers and regions are exaggerated for clarity.

Hereinafter, embodiments of the present invention will be described with reference to drawings that are schematic illustrations of idealized embodiments. In the drawings, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing.

Figure 1:
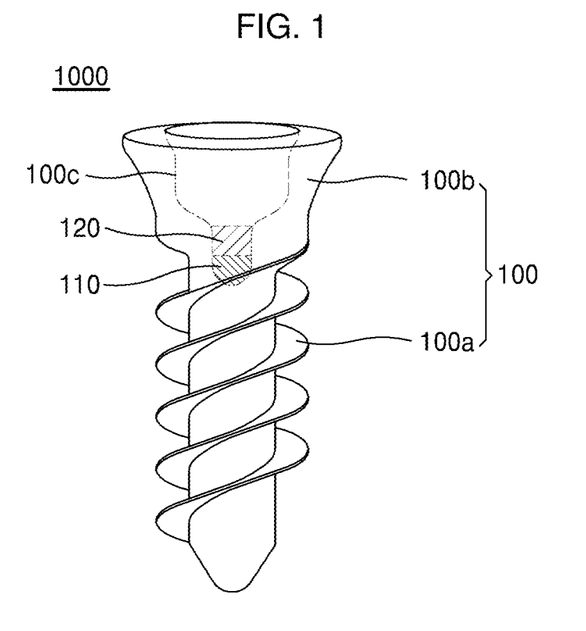
FIGS. 1 and 2 are diagrams illustrating structures of an implant according to an embodiment of the present invention.

FIG. 1 is a diagram illustrating a structure of an implant according to a first embodiment of the present invention. Referring to FIG. 1, an implant 1000 according to an embodiment of the present invention includes a body 100 having a groove, a first filling metal 110 filling at least one portion of a lower region of the groove, and a second filling metal 120 filling in the groove on the first filling metal 110.

As shown in FIG. 1, the body 100 may have a screw shape including a thread portion 100a at a lower portion and a head portion 100b at an upper portion. The groove 100c formed in the body 100 has a shape extending vertically downward from a top surface of the body 100 with a predetermined depth. For example, the groove 100c may have a shape recessed vertically downward from the top surface of the head portion 100b toward the treaded portion 100a by the predetermined depth.

The groove 100c may have a structure in which a cross-sectional area of an upper region is different from that of a lower region in the vertical direction. For example, as shown in FIG. 1, the groove 100c includes the upper region having a first cross-sectional area and a first depth and a lower region having a second cross-sectional area smaller than the first cross-sectional area and a second depth. In this case, the groove 100c may have a portion having a tapered shape with gradually increasing cross-sectional areas from the lower region to the upper region. In this regard, the upper region and the lower region are relative concepts to divide the space inside the groove 100c. When a portion of the space inside the groove 100c is defined as the lower region, another portion of the space inside the groove 100c upper than the lower region may be defined as the upper region.

The body 100 constituting the implant 1000 is formed of a metallic material suitable for use in a living body, specifically, selected from titanium (Ti), a Ti alloy, stainless steel, and a cobalt-chromium (Co—Cr) alloy.

The first filling metal 110 may fill a portion inside of the groove 100c. For example, as shown in FIG. 1, the first filling metal 110 may fill a portion of the lower region of the groove 100c. The second filling metal 120 may fill the groove 100c on the first filling metal 110. Thus, the first filling metal 110 and the second filling metal 120 may be vertically stacked in the groove. The first filling metal 110, the second filling metal 120, and the body 100 are in direct contact with each other to be in electrical contact with each other.

The first filling metal 110 and the second filling metal 120 may be different metals having different ionization tendencies.

For example, one of the first filling metal 110 and the second filling metal 120 may be zinc (Zn) or a Zn alloy, and the Zn alloy may include a zinc-calcium (Zn—Ca) alloy. The other may be magnesium (Mg) or a Mg alloy, for example, a magnesium-calcium (Mg—Ca) alloy which have a higher ionization tendency.

As another example, when one of the first filling metal 110 and the second filling metal 120 is iron (Fe) or a Fe alloy, the other is Zn, a Zn alloy, Mg, or a Mg alloy.

As another example, the first filling metal 110 and the second filling metal 120 may be metals of the same type having different ionization tendencies. For example, one of the first filling metal 110 and the second filling metal 120 may be a pure metal, and the other may be an alloy including the pure metal as a main metal. Alternatively, the first filling metal 110 and the second filling metal 120 may be alloys of the same type including the same main metal and having different composition ratios. For example, the first filling metal 110 may be pure Zn, Fe, or Mg, and the second filling metal 120 may be a Zn alloy, an Fe alloy, or a Mg alloy each having a higher ionization tendency that that of the pure metal. Also, the reverse is possible.

Alternatively, the first filling metal 110 may be one Zn alloy, Fe alloy, or Mg alloy, and the second filling metal 120 may be another Zn alloy, Fe alloy, or Mg alloy each having a different composition ratio and a different ionization tendency than those of the first filling metal 110.

Meanwhile, both the first filling metal 110 and the second filling metal 120 have higher ionization tendencies than that of the body 100. Thus, galvanic corrosion may occur between the first filling metal 110 and the body 100 or between the second filling metal 120 and the body 100. The implant 1000 having the above-described configuration is in a corrosion environment after being implanted into a human body via a surgical procedure. In this case, the first filling metal 110 or the second filling metal 120 functions as an anode, and the body 100 functions as a cathode, thereby causing galvanic corrosion.

As shown in FIG. 1, since a space above the second filling metal 120 is empty, a top surface of the second filling metal 120 is directly exposed to an external environment where corrosion occurs. Thus, corrosion occurs first on the top surface of the second filling metal 120.

A method of controlling a generation amount of reactive oxygen species after a surgical placement of the implant 1000 using the ionization tendency difference between the first filling metal 110 and the second filling metal 120 of the implant 1000 having the above-described configuration will be described.

Hereinafter, a behavior an implant in which an ionization tendency of the second filling metal 120 is higher than an ionization tendency of the first filling metal 110 will be described.

First, galvanic corrosion occurs due to an ionization tendency difference between the second filling metal 120 and the body 100. In this case, electrochemically, the second filling metal 120 functions as an anode, and the body 100 functions as a cathode. For example, when the second filling metal 120 is Mg and the body 100 is a titanium (Ti) alloy, hydrogen peroxide ($H_2O_2$), as one of the reactive oxygen species, is generated according to the following reaction between the second filling metal 120 functioning as the anode and the body 100 functioning as the cathode.

Anode:

Cathode:

In this regard, due to a high corrosion rate of the second filling metal 120, the generation rate of reactive oxygen species (ROS generation rate) increases, so that a large amount of reactive oxygen species may be generated.

When corrosion of the second filling metal 120 is completed, the second filling metal 120 disposed on the first filling metal 110 is exhausted. As the second filling metal 120 is removed, a top surface of the first filling metal 110 is directly exposed to the corrosion environment, and corrosion occurs thereon. Thus, a stage of completion of corrosion of the second filling metal 120 may be understood as a stage of initiation of corrosion of the first filling metal 110. However, at the time when the consumption of the second filling metal 120 is completed, the remaining second filling metal 120 and an exposed portion of the first filling metal 110 may simultaneously be corroded.

When corrosion of the first filling metal 110 is initiated, reactive oxygen species are generated under the same principle of that of the second filling metal 120. However, since the first filling metal 110 is formed of a material having a lower ionization tendency than that of the second filling metal 120, a corrosion rate is relatively low when galvanic corrosion occurs between the body 100 and the first filling metal 110. Thus, the ROS generation rate on the surface of the body 100 functioning as the cathode is relatively low compared with that when the second filling metal 120 is corroded due to a relatively lower corrosion rate than that of the second filling metal 120. Therefore, a generation amount of the reactive oxygen species decreases.

Thus, a method of controlling the generation rate of reactive oxygen species after a surgical placement of the implant is realized by using the implant according to the first embodiment. That is, according to the method, the generation rate of reactive oxygen species is controlled using an implant including a first filling metal and a second filling metal both having higher ionization tendencies than that of the body. The method includes a first step of generating reactive oxygen species by ionization of the second filling metal caused by galvanic corrosion between the second filling metal and the body, and then a second step of generating reactive oxygen species in a lower concentration than that of the first step by ionization of the first filling metal caused by galvanic corrosion between the first filling metal and the body.

In the case of the implant according to the first embodiment of the present invention, reactive oxygen species are produced in a high concentration at an early stage of the surgical procedure due to a high ROS generation rate. However, the ROS generation rate decreases over time, and thus the process enters a step of producing reactive oxygen species in a relatively low concentration.

Therefore, when an implant procedure according to an embodiment of the present invention is performed, osteomyelitis, periodontal disease, gum inflammation, and the like frequently caused by infection at an early stage of the procedure may be prevented by generating reactive oxygen species in a concentration sufficient for antimicrobial defense action. After the risk of infection caused by implantation surgery decreases, the concentration of the generated reactive oxygen species may be reduced and maintained at a low level enough for neo-angiogenesis. Accordingly, antimicrobial defense function and angiogenesis inducing function, which are two major functions of reactive oxygen species, may be controlled according to the healing step of the operation site by time only using a single implant.

If required, reactive oxygen species may be generated in a low concentration at the initial stage and then the concentration may be increased to a high concentration over time. In this case, a metal having a lower ionization tendency than that of the first filling metal 110 may be used as the second filling metal 120.

The implant according to the first embodiment may be manufactured by sequentially inserting a first filling metal member and a second filling metal member into the groove formed inside the implant.

For example, the first and second filling metal members having similar shapes and sizes to the region for insertion inside the groove may be prepared and inserted into the groove by applying mechanical pressure to the first and second filling metal members.

For example, when the first and second filling metal members are inserted by press-fit, they are brought into contact with the inner surface of the groove with slight plastic deformation of the first and second filling metal members in the inserting stage, thereby forming stable mechanical bond therebetween.

As another manufacturing method, casting may be used. For example, an appropriate amount of a molten fluid of the first filling metal is injected into the groove of the body and solidified. Then, a molten fluid of the second filling metal is inserted into the empty space above the first filling metal and solidified to complete the manufacturing.

As another manufacturing method, powder metallurgy may be used. For example, powder of the first filling metal is introduced into the groove and subjected to first sintering, and powder of the second filling metal is introduced thereon and subjected to second sintering to manufacture the first filling metal and the second filling metal. Alternatively, the groove may be filled sequentially with the first filling metal powder and the second filling metal powder and the powders are simultaneously sintered.

Figure 2:
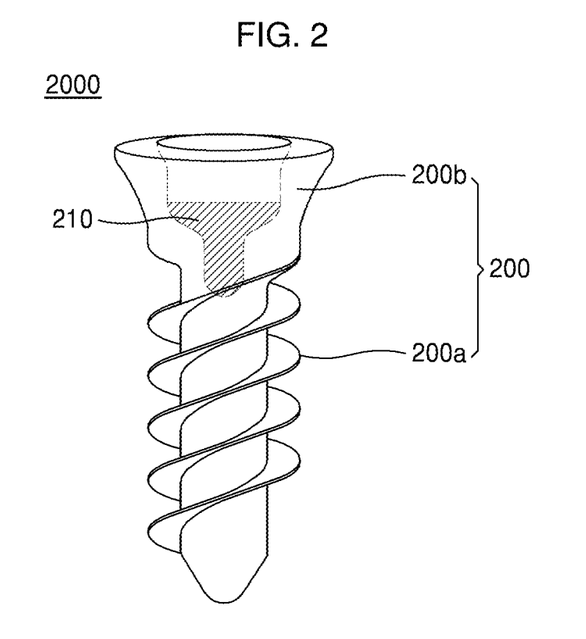

FIG. 2 is a diagram illustrating a structure of an implant according to a second embodiment. In the following descriptions about the second embodiment, those described above will not be repeated for descriptive convenience.

Referring to FIG. 2, an implant 2000 may include a body 200 having a groove and a filling metal 210 inserted into the groove. In this regard, the filling metal 210 is a metal having a higher ionization tendency than that of the body 200. Thus, galvanic corrosion may occur between the filling metal 210 and the body 200.

The groove may have a structure in which a cross-sectional area of an upper region is larger than that of a lower region, and the filling metal 210 may fill up to at least one portion of the upper region having the larger cross-sectional area. The filling metal 210 may be a biodegradable metal such as Zn, a Zn alloy, Mg, or a Mg alloy.

When a surgical procedure of the implant 2000 having the above-described configuration is performed, corrosion starts from a top surface of the filling metal 210 by galvanic corrosion in a corrosion environment. Since the upper region has a larger corrosion area due to a larger cross-sectional area than the lower region, a large number of free electrons are generated, thereby increasing the ROS generation rate. Since the lower region has a smaller cross-sectional area where corrosion occurs, a small number of free electrons are generated, thereby having a relatively low ROS generation rate.

Therefore, a method of controlling a generation rate of reactive oxygen species after the procedure using the implant according to the second embodiment is provided. That is, the method includes a first step of generating reactive oxygen species by ionization of the filling metal 210 having a larger first cross-sectional area, and then a second step of generating reactive oxygen species in a lower concentration than that of the first step by ionization of the filling metal 210 having a second cross-sectional area smaller than the first cross-sectional area after the first step.

According to the second embodiment, as in the first embodiment, the concentration of reactive oxygen species may be controlled with time, thereby obtaining both the function of preventing infection caused by a surgical procedure and inducing angiogenesis.

As a modified example of the second embodiment, the upper and lower regions of the second embodiment may have opposite cross-sectional areas. That is, the groove may include an upper region having a cross-sectional area smaller than a cross-sectional area of a lower region, and a filling metal may fill up to at least one portion of the upper region having the smaller cross-sectional area. In this case, contrary to the second embodiment, the concentration of reactive oxygen species generated in the second step may be greater than that of reactive oxygen species generated in the first step.

Hereinafter, the present invention will be described in more detail according to the following examples. However, the following examples are merely presented to exemplify the present invention and the present invention is not limited thereto.

Preparation Example 1. Preparation of Implant Filled with Zn/Mg

An implant filled with Zn/Mg capable of controlling a generation rate of reactive oxygen species was prepared. Specifically, a Zn member was mechanically inserted onto the bottom of the implant and filled up to a certain region. Subsequently, Mg was filled on the Zn layer up to a region inside the implant immediately before the cross-sectional area starts to increase.

Preparation Example 2. Preparation of Implant Filled with Zn

An implant filled with Zn was prepared to control a generation rate of reactive oxygen species. Zn was filled in the same manner as in Preparation Example 1 from the bottom to a certain region. Then, Zn was further filled thereon up to a region in the implant where the cross-sectional area starts to increase in the same manner.

Figure 3A:
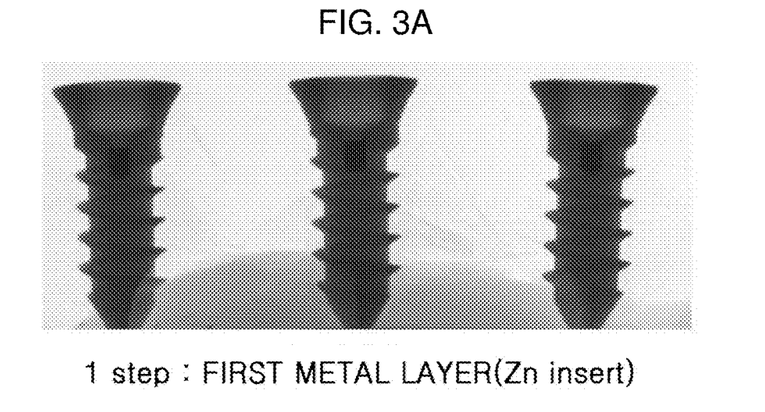
FIGS. 3A and 3B are micro-computed tomography (CT) images of an implant filled with a first filling metal and a second filling metal according to an embodiment of the present invention.
Figure 3B:
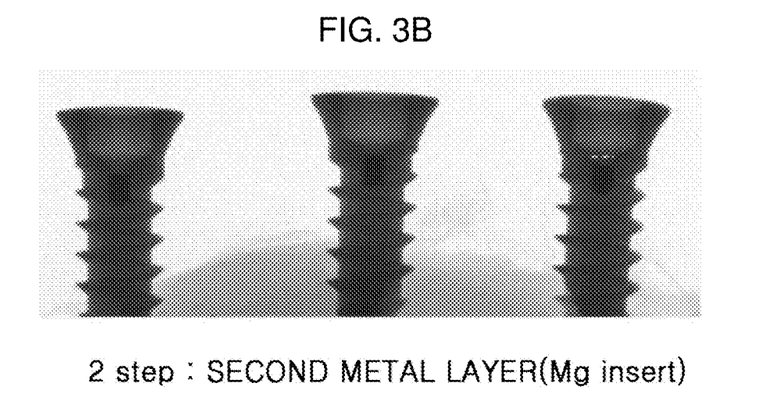

FIGS. 3A and 3B are micro-computed tomography (CT) images of the implant filled with Zn/Mg according to Preparation Example 1.

FIG. 3A shows an implant having an Zn layer filled therein, and it is confirmed that the Zn layer is formed from the bottom of the implant to a certain region as shown as a black portion in the micro-CT image. FIG. 3B is a micro-CT image obtained after filling Mg, and it is confirmed that an Mg layer is formed on the Zn layer (The surface of Mg is not clear in the micro-CT and marked with a white dotted line).

Figure 4A:
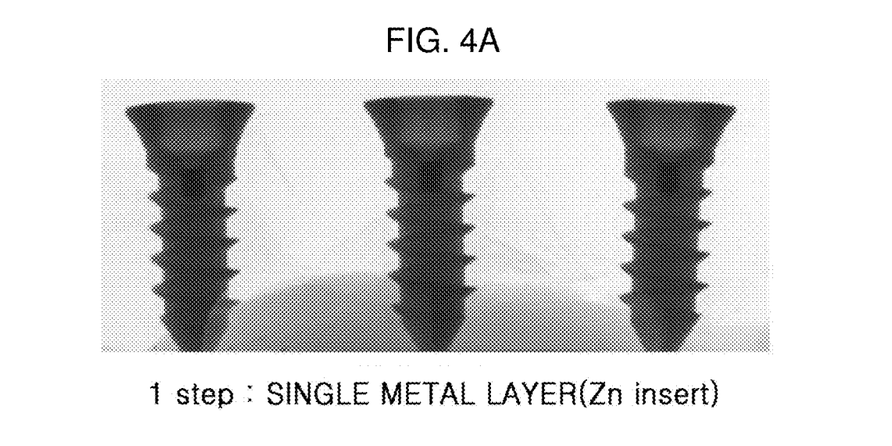
FIGS. 4A and 4B are micro-CT images of an implant according to an embodiment of the present invention in which a metal is filled up to a portion where a cross-sectional area starts to increase.
Figure 4B:
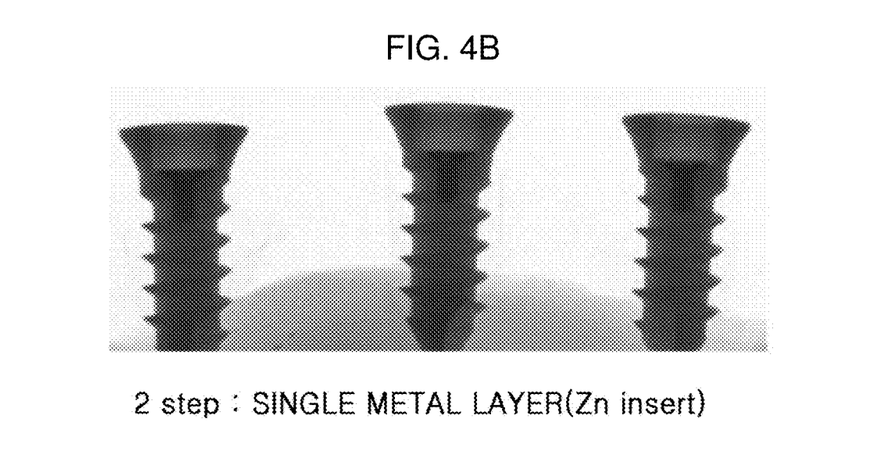

FIGS. 4A and 4B are micro-CT images of the implant filled with Zn according to Preparation Example 2.

FIG. 4A shows that an implant having a Zn layer filled therein by the first step, and it is confirmed that the Zn layer is formed from the bottom to a certain region as shown as a black portion in the micro-CT image. In addition, FIG. 4B is a micro-CT image obtained after further filling the implant with Zn, it is confirmed that Zn fills up to a region in the implant where the cross-sectional area starts to increase.

Figure 5:
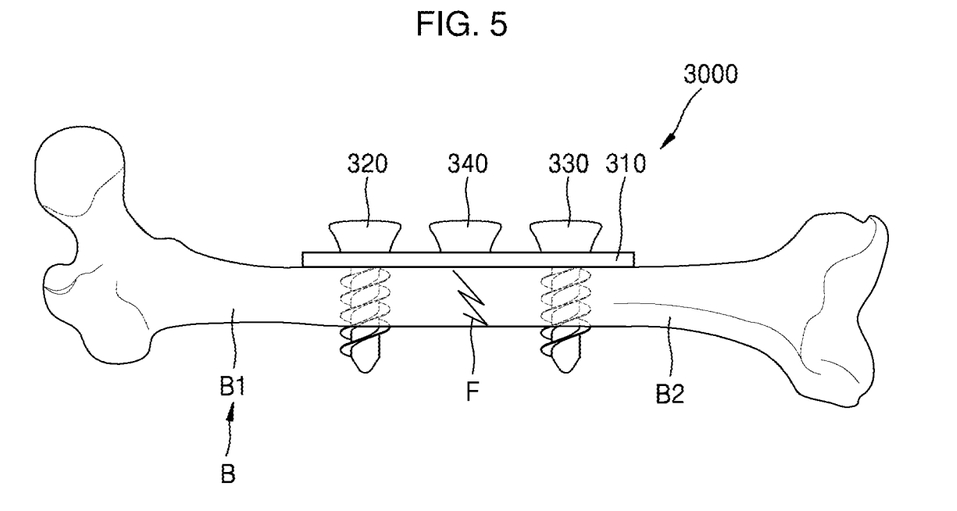
FIG. 5 is a cross-sectional view schematically illustrating a fracture fixation device according to an embodiment of the present invention which fixes a fracture site of a bone.
Figure 6:
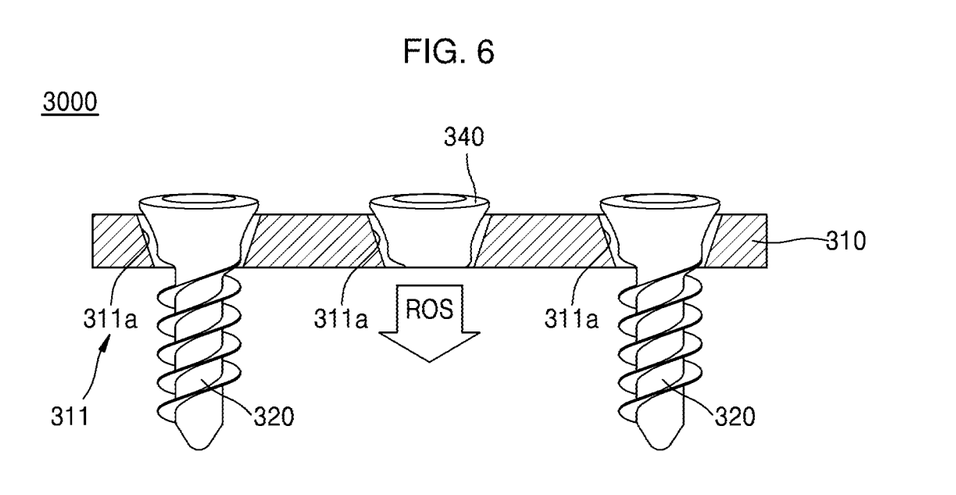
FIG. 6 is a cross-sectional view illustrating the fracture fixation device of FIG. 5 in more detail.
Figure 7:
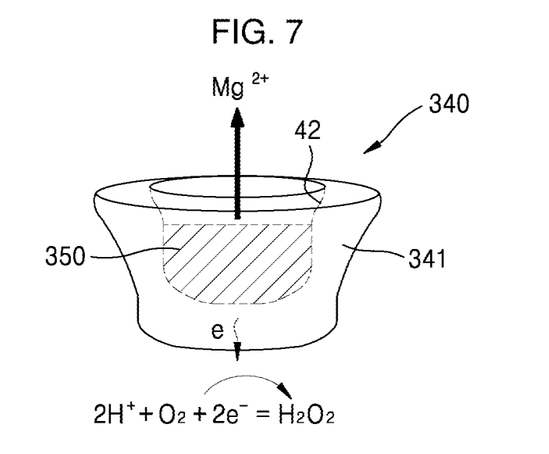
FIGS. 7 to 9 are cross-sectional views schematically illustrating examples of a functional implant of the fracture fixation device of FIG. 1.
Figure 8:
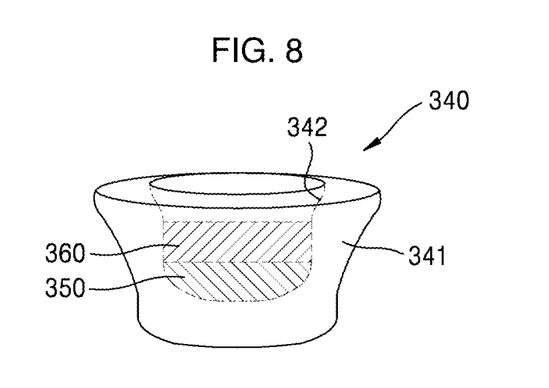

FIG. 5 is a cross-sectional view schematically illustrating a fracture fixation device 3000 according to an embodiment of the present invention which fixes a fracture site F of a bone B. FIG. 6 is a cross-sectional view illustrating the fracture fixation device 3000 of FIG. 5 in more detail. FIGS. 7 and 8 are cross-sectional views schematically illustrating examples of a functional implant 340 of the fracture fixation device 3000 of FIG. 5.

First, referring to FIGS. 5 and 6, the fracture fixation device 3000 according to an embodiment of the present invention includes a fixation plate 310, a first fixing implant 320, a second fixing implant 330, and a functional implant 340.

As shown in FIGS. 5 and 6, the fixation plate 310 is disposed on at least one portion of a broken bone B and has a plurality of implant holes 311 formed at intervals. More specifically, the fixation plate 310 may be used at a position corresponding to the fracture site F of the bone B such that a first fracture part B1 and a second fracture part B2 of the broken bone B are maintained in a firmly fixed state via engagement respectively with the first fixing implant 320 and the second fixing implant 330 which will be described below.

In addition, the fixation plate 310 may be formed of a metallic material harmless to the human body to maintain the firmly fixed state in accordance with the fracture site F of the bone B. In addition, the fixation plate 310 is formed of a dynamic compression plate (DCP) which may be molded in a shape of a patient's bone B during a surgical procedure to be in close contact with the fracture site F.

As shown in FIGS. 5 and 6, the first fixing implant 320 may penetrate one of the plurality of implant holes 311 of the fixation plate 310 to be inserted into the first fracture part B1 in order to fix the first fracture part B1 of the bone B. Also, the second fixing implant 330 may penetrate another implant hole 311 of the fixation plate 310 to be inserted into the second fracture part B2 to fix the second fracture part B2 of the bone B.

For example, the first fracture part B1 and the second fracture part B2 of the broken bone B may be firmly fixed with respect to the fracture site F by disposing the fixation plate 310 at a position corresponding to the fracture site F of the broken bone B, fixing the first fracture part B1 by inserting the first fixing implant 320 into an implant hole 311 of the fixation plate 310 formed at a position corresponding to the first fracture part B1 of the bone B, and fixing the second fracture part B2 by inserting the second fixing implant 330 into another implant hole 311 of the fixation plate 310 formed at a position corresponding to the second fracture part B2.

More specifically, the first fixing implant 320 and the second fixing implant 330 may be inserted respectively into the first fracture part B1 and the second fracture part B2 by self-penetrating and may have a flat head screw shape including a head portion with an inclined plane corresponding to an inclined plane 311a of the implant hole 311 of the fixation plate 310. Therefore, the first fixing implant 320 and the second fixing implant 330 are inserted into the bone B in a state where the inclined planes of the head portions of the first fixing implant 320 and the second fixing implant 330 press the inclined planes 311a of the implant holes 311 of the fixation plate 310, leading to more firmly fix the fixation plate 310 to the bone B.

Also, the first fixing implant 320 and the second fixing implant 330 may be formed of a metallic material harmless to the human body such that each of the first and second fracture parts B1 and B2 is inserted into the bone B by self-penetrating and maintained in a firmly fixed state. For example, the fixation plate 310, the first fixing implant 320, and the second fixing implant 330 may be formed of at least one metallic material selected from Ti, a Ti alloy, stainless steel, and a cobalt-chromium (Co—Cr) alloy as the metallic material suitable for use in the human body.

However, the materials and shapes of the fixation plate 310, the first fixing implant 320, and the second fixing implant 330 are not limited thereto and may be modified according to a state of a patient or selection by a practitioner.

As described above, the fracture fixation device 3000 may easily fix the first fracture part B1 and the second fracture part B2 in a firmly fixed state during a healing time for healing the fracture site F of the bone B by engaging the first fracture part B1 and the second fracture part B2 of the broken bone B to maintain fixed positions thereof using the fixation plate 310, the first fixing implant 320, and the second fixing implant 330.

In this regard, the number of the implant holes 311 formed in the fixation plate 310 or the number of fixing implants 320 and 330 are not limited to the above-described embodiments and may be modified to various numbers according to a region or area of a broken or damaged bone B. For example, although three implant holes 311 are formed in the fixation plate 310 and two fixing implants 320 and 330 are used according to the present embodiment, four or more implant holes 311 may be formed in the fixation plate 310 and fixation screws are engaged into all implant holes 311 or selectively engaged into some implant holes 311.

In this regard, among the plurality of implant holes 311 formed in the fixation plate 310, an implant hole 311 adjacent to a position corresponding to the fracture site F of the bone B is generally kept empty without any fixing screw inserted therein although this may vary according to characteristics of the fracture site F. However, the fracture site F may be a site where the reactive oxygen species are needed most for rapid angiogenesis and regeneration of the broken or damaged bone B.

Thus, the fracture fixation device 3000 according to an embodiment of the present invention may shorten the healing time for fracture by inducing angiogenesis in hematomas of the fracture site F by inducing generation of reactive oxygen species in the fracture site F of the bone B by inserting a functional implant 340 capable of promoting regeneration of the fracture site F into an implant hole 311 of the fixation plate 310 adjacent to a position corresponding to the fracture site F of the bone B.

For example, as shown in FIGS. 5 and 6, the functional implant 340 only includes a head portion having a flat head screw shape without a threaded portion that extends downward from the head portion and inserted into at least one portion of the bone. The functional implant 340 is disposed in the implant hole 311 of the fixation plate 310 and a lower surface thereof is disposed above the fracture site F.

The functional implant 340 plays a role in generating reactive oxygen species and supplying the generated reactive oxygen species to the fracture site F. The reactive oxygen species supplied to the fracture site F are diffused to hematomas and promote angiogenesis of the fracture site F, thereby promoting conglutination of the fracture site F resulting in shortening the healing time of fracture.

The functional implant 340 may generate reactive oxygen species as galvanic corrosion occurs between different metals having different ionization tendencies and filling the functional implant 340 to generate reactive oxygen species.

For example, as illustrated in FIG. 7, the functional implant 340 may include a body 341 formed in a shape corresponding to the implant hole 311 of the fixation plate 310 and inserted into the implant hole 311 and a recessed portion 342 recessed from a surface of the body 341 such that a metal different from a material used to form the body 341 fills the recessed portion 342.

The body 341 may be formed of a metallic material suitable for use in the human body, such as Ti, a Ti alloy, stainless steel, and a cobalt-chromium (Co—Cr) alloy and may be inserted into the implant hole 311 of the fixation plate 310 by screw coupling, bonding coupling, or press-fitting coupling.

Also, as shown in FIG. 7, at least one region of the recessed portion 342 of the functional implant 340 may be filled with a first filling metal 350 having an ionization tendency higher than the metallic material used to form the body 341. For example, the first filling metal 350 may be a biodegradable metal such as Zn, a Zn alloy, Mg, or a Mg alloy.

When the functional implant 340 is formed as described above, electrochemically, the first filling metal 350 functions as an anode and the body 341 functions as a cathode. For example, when the first filling metal 350 is Mg, hydrogen peroxide ($H_2O_2$) as one of the reactive oxygen species is generated according to the following reaction between the first filling metal 350 functioning as the anode and the body 341 functioning as the cathode.

$$Mg+2H_2O \rightarrow Mg(OH)_2+2H^++2e^- \qquad \text{Anode:}$$

$$O_2+2H^++2e^- \rightarrow H_2O_2 \qquad \text{Cathode:}$$

As illustrated in FIG. 5, the functional implant 340 is disposed to be adjacent to an upper portion of the fracture site F, and thus reactive oxygen species generated by galvanic corrosion between the body 341 and the first filling metal 350 of the functional implant 340 are diffused to hematomas of the fracture site F adjacent thereto. Thus, angiogenesis of the fracture site F is induced to promote healing of the fracture site F, resulting in shortening the healing time of fracture.

Meanwhile, referring to FIG. 6, the functional implant 340 is in direct contact with the fixation plate 310. When the fixation plate 310 is formed of a metallic material, the functional implant 340 and the fixation plate 310 are in electrical communication with each other. In this case, in addition to the body 341 of the functional implant 340, the cathode is extended to the fixation plate 310 electrically connected thereto.

In this case, reactive oxygen species may be generated from the entire surface of the fixation plate 310 and supplied to the bone B in contact with the fixation plate 310.

Although a large amount of reactive oxygen species may be helpful for preventing infection by bacteria immediately after a surgical procedure, the amount of reactive oxygen species required for neo-angiogenesis and/or the healing process of the fracture site F therefor may decrease as the healing process of the fracture site F proceeds. Thus, the functional implant 340 may be designed such that the generation rate of reactive oxygen species decreases over time as the healing process of the fracture site F of the bone B proceeds.

For example, according to an embodiment, the ROS generation rate may be controlled using a plurality of metals filling the recessed portion 342 and having different ionization tendencies as shown in FIG. 8.

More specifically, a second filling metal 360 having an ionization tendency higher than that of the first filling metal 350 may fill the recessed portion 342 of the functional implant 340 to be disposed on the first filling metal 350. For example, when the first filling metal 350 is formed of Zn or a Zn alloy, the second filling metal 360 may be formed of Mg or a Mg alloy having a higher ionization tendency. Also, as another example, when the first filling metal 350 is formed of Fe or a Fe alloy, the second filling metal 360 may be formed of one of Zn, a Zn alloy, Mg, and a Mg alloy having a higher ionization tendency.

Accordingly, as shown in FIG. 8, the top surface of the second filling metal 360 is directly exposed to the external corrosion environment. Thus, corrosion occurs preferentially on the top surface of the second filling metal 360.

As such, when the functional implant 340 is formed, electrochemically, the second filling metal 360 functions as an anode, and the body 341 functions as a cathode.

In this case, a high corrosion rate of the second filling metal 360 may increase the ROS generation rate, resulting in generation of a large amount of reactive oxygen species.

Upon completion of corrosion of the second filling metal 360, the second filling metal 360 filled on the first filling metal 350 may be exhausted. As the second filling metal 360 is removed as described above, the top surface of the first filling metal 350 is exposed to the corrosion environment and corrosion occurs. Therefore, a stage of completion of corrosion of the second filling metal 360 may be understood as a stage of initiation of corrosion of the first filling metal 350. However, at a time when the removal of the second filling metal 360 is completed, corrosion of the remaining second filling metal 360 and an exposed upper portion of the first filling metal 350 may simultaneously occur.

When corrosion of the first filling metal 350 is initiated, reactive oxygen species are generated under the same principle of that of the second filling metal 360. However, since the first filling metal 350 is formed of a material having a lower ionization tendency than that of the second filling metal 360, the ROS generation rate of the first filling metal 350 may be relatively low due to the lower corrosion rate than that of the second filling metal 360 when compared with that of the second filling metal 360. Therefore, the generation amount of reactive oxygen species may decrease.

Accordingly, a method of controlling the generation amount of reactive oxygen species after a surgical procedure using a functional implant according to the above-described embodiment is provided. That is, the method may include a first step of generating reactive oxygen species by ionization of the second filling metal 360 having a higher ionization tendency than that of the first filling metal 350, and a second step of generating reactive oxygen species in a lower concentration than that of the first step by ionization of the first filling metal 350.

In the case of the fracture fixation device including the functional implant according to an embodiment of the present invention, the generation of reactive oxygen species is controlled by increasing the ROS generation rate at an early stage of healing of the fracture site F when a large amount of reactive oxygen species is required for antibacterial function against infection and unnecessary supply of reactive oxygen species may be reduced after the healing process of the fracture site F considerably proceeds.

Figure 9:
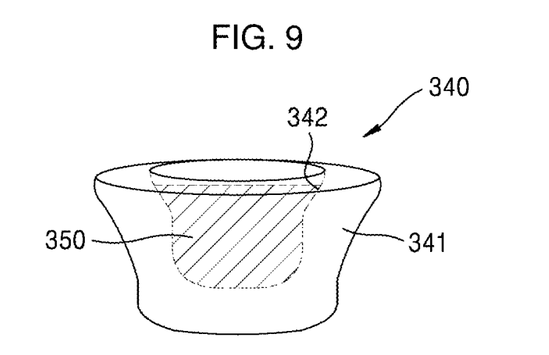

As another example, the effect on controlling generation of reactive oxygen species may be obtained by changing the cross-sectional area of the first filling metal 350.

Specifically, referring to FIG. 9, the recessed portion 342 filled with the first filling metal 350 includes an upper region having a cross-sectional area larger than that of a lower region, and the first filling metal 350 may fill at least one portion of the upper region having the larger cross-sectional area. Here, the upper region and the lower region are relative concepts to divide the space inside the recessed portion. When a portion of the space inside the recessed portion is defined as the lower region, another portion of the space inside the recessed portion vertically upper than the lower region may be defined as the upper region.

For example, as shown in FIG. 9, the recessed portion 342 may have a portion having a tapered shape with gradually increasing cross-sectional areas from the lower region to the upper region. As another example, the recessed portion 342 may be formed to have a trapezoidal cross-sectional area in which a length of the upper side is greater than a length of the lower side. Also, the recessed portion 342 may be formed in various shapes with decreasing transverse cross-sectional areas from a upper region to a lower region, e.g., a shape with an inverted triangular longitudinal cross-sectional area, a shape with a step shaped longitudinal cross-sectional area, or a shape with a funnel shaped longitudinal cross-sectional area.

The first filling metal 350 may be a biodegradable metal such as Zn, a Zn alloy, Mg, or a Mg alloy.

When the functional implant 340 having the above-described configuration is used, corrosion occurs from the top surface of the first filling metal 350 in the corrosion environment. Since the upper region has a larger corrosion area due to a larger cross-sectional area, large number of electrons are generated, thereby increasing the ROS generation rate. Since the lower region has a smaller cross-sectional area where corrosion occurs, small amount of free electrons are generated, thereby having a relatively lower ROS generation rate.

Therefore, a method of controlling the generation rate of reactive oxygen species after the procedure using the functional implant according to the above-described embodiment is provided. That is, the method includes a first step of generating reactive oxygen species by ionization of the first filling metal having a larger first cross-sectional area, and then a second step of generating reactive oxygen species in a lower concentration than that of the first step by ionization of the first filling metal having a second cross-sectional area smaller than the first cross-sectional area after the first step.

Figure 10:
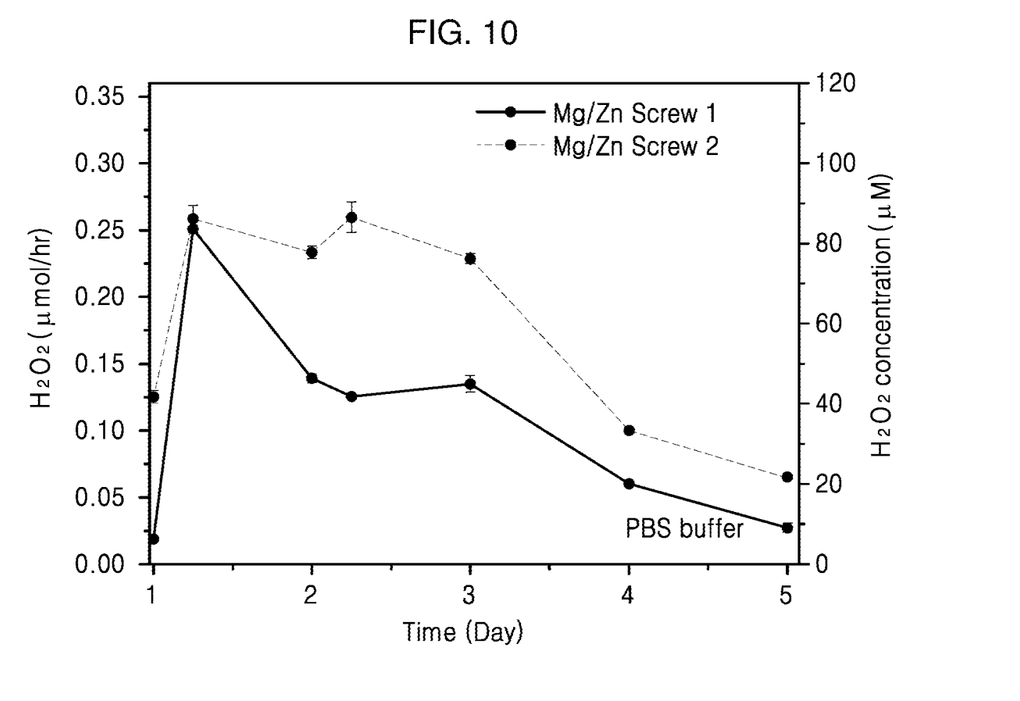
FIGS. 10 and 11 are graphs illustrating generation rates of reactive oxygen species according to an embodiment of the present invention.
Figure 11:
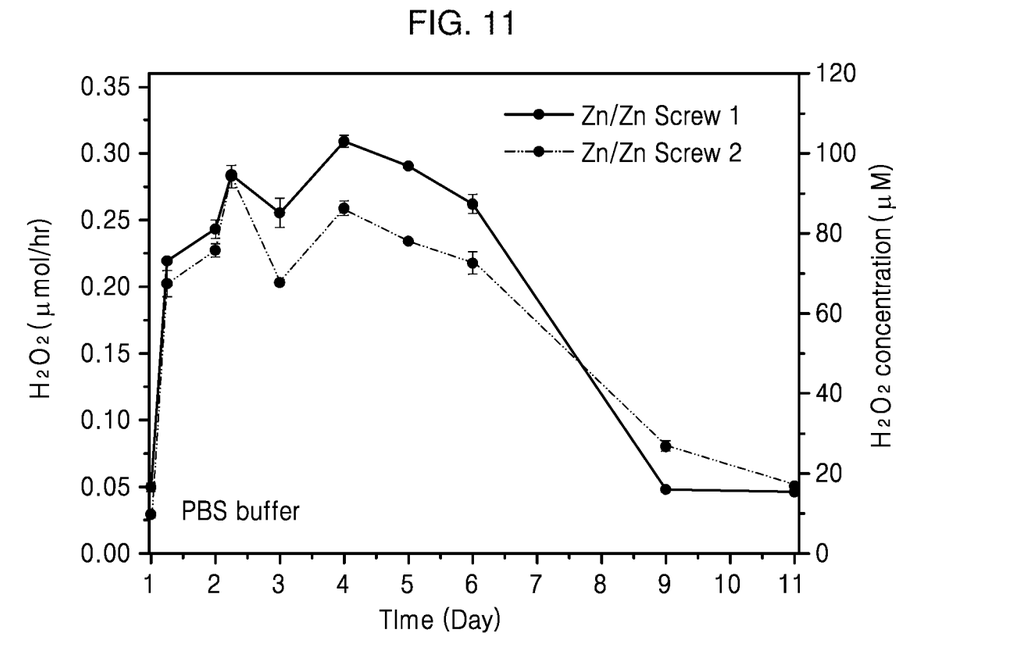

FIGS. 10 and 11 are graphs illustrating the generation rates of reactive oxygen species according to an embodiment of the present invention.

FIG. 10 is a graph illustrating concentrations of reactive oxygen species over time after adding a body in a PBS buffer, the body formed of titanium and having a recessed portion filled with Zn as a first filling metal and Mg as a second filling metal.

Referring to FIG. 10, it is confirmed that reactive oxygen species are generated with a rate of 0.25 µmol/h for about 2 days, and then the generation rate of the reactive oxygen species gradually decreases at day and thereafter. It is considered that the concentration of reactive oxygen species in a PBS buffer rapidly increases for about 2 days as a large amount of reactive oxygen species is generated by corrosion of Mg, and the concentration of reactive oxygen species decreases at day 2 and thereafter since corrosion of Zn is initiated and the generation rate of reactive oxygen species by Zn is lower than that of Mg.

FIG. 11 is a graph illustrating the generation rate of reactive oxygen species over time after adding a body in a PBS buffer, the body formed of Ti and having a recessed portion in which a lower region is primarily filled with Zn and a upper region having a larger cross-sectional area than that of the lower region previously filled with Zn is secondarily filled with Zn.

Referring to FIG. 11, it is confirmed that reactive oxygen species are generated with a rate of 0.3 µmol/h for 4 days and the generation rate of the reactive oxygen species gradually decreases at day 5 and thereafter as a result of measuring the concentrations of the reactive oxygen species in a PBS buffer over time after adding the implant filled with Zn of Preparation Example 2 in the PBS buffer.

It is considered that the concentration of reactive oxygen species is high for about 4 days since a large amount of reactive oxygen species is generated due to a large cross-sectional area of Zn exposed to the PBS buffer, and the concentration of reactive oxygen species decreases since a smaller amount of reactive oxygen species is generated due to a small cross-sectional area of Zn exposed to the PBS buffer.

The fracture fixation device 3000 according to various embodiments of the present invention may induce generation of reactive oxygen species in a fracture site F of a bone B broken by external impact and control the generation of reactive oxygen species by increasing the ROS generation rate at an early stage of healing of the fracture site F when a large amount of reactive oxygen species is required for antibacterial function against infection and decreasing the ROS generation rate when the healing of the fracture site F is almost completed.

According to an embodiment of the present invention as described above, the implant having the anti-infective action against bacteria and angiogenesis inducing function by controlling the ROS generation rate and the method of manufacturing the same are provided. However, these problems to be solved are illustrative and the scope of the present invention is not limited thereby.

While one or more embodiments of the present invention have been described with reference to the drawings, it will be understood by those of ordinary skill in the art that various changes in form and details may be made therein without departing from the spirit and scope of the present invention as defined by the following claims.

What is claimed is:

1. An implant having a controlled generation rate of reactive oxygen species, the implant comprising:
    a body made of a metallic material and having a groove;
    a first filling metal filling a region inside the groove; and
    a second filling metal filling the groove on the first filling metal,
    wherein the second filling metal has an ionization tendency different from that of the first filling metal, and
    both the first filling metal and the second filling metal have ionization tendencies higher than that of the body.

2. The implant of claim 1, wherein the second filling metal has a higher ionization tendency than that of the first filling metal.

3. The implant of claim 1, wherein one of the first filling metal and the second filling metal is zinc (Zn) or a Zn alloy, and the other is magnesium (Mg) or a Mg alloy.

4. The implant of claim 1, wherein one of the first filling metal and the second filling metal is iron (Fe) or a Fe alloy, and the other is Zn, a Zn alloy, Mg, or a Mg alloy.

5. The implant of claim 1, wherein one of the first filling metal and the second filling metal is a pure metal, and the other is an alloy including the pure metal as a main metal.

6. The implant of claim 1, wherein the first filling metal and the second filling metal are alloys including the same main metal and having different composition ratios.

7. The implant of claim 1, wherein the body comprises one selected from titanium (Ti), a Ti alloy, stainless steel, and a cobalt-chromium (Co—Cr) alloy.

8. The implant of claim 1, wherein the groove has a shape extending vertically downward from a top surface of the body with a predetermined depth.

9. An implant having a controlled generation rate of reactive oxygen species, the implant comprising:
    a body made of a metallic material and having a groove; and
    a filling metal filling at least one region inside the groove,
    wherein the groove comprises an upper region having a cross-sectional area different from a cross-sectional area of a lower region,
    the filling metal fills at least one portion of the upper region having the different cross-sectional area, and
    the filling metal has a higher ionization tendency than that of the body.

10. The implant of claim 9, wherein the cross-sectional area of the lower region is smaller than the cross-sectional area of the upper region.

11. The implant of claim 10, wherein the groove comprises a portion in which a cross-section increases in a tapered shape from the lower region to the upper region.

12. The implant of claim 9, wherein the filling metal is zinc (Zn), a Zn alloy, magnesium (Mg), or a Mg alloy.

13. The implant of claim 9, wherein the body is formed of titanium (Ti), a Ti alloy, stainless steel, or a cobalt-chromium (Co—Cr) alloy.

14. The implant of claim 9, wherein the groove has a shape extending vertically downward from a top surface of the body with a predetermined depth.

15. A method of controlling a generation rate of reactive oxygen species using an implant comprising a first filling metal and a second filling metal both having higher ionization tendencies than that of a body, the method comprising:
a first step of generating reactive oxygen species by ionization of the second filling metal caused by galvanic corrosion between the second filling metal and the body; and
a second step of generating reactive oxygen species in a concentration different from a concentration of reactive oxygen species obtained in the first step by ionization of the first filling metal caused by galvanic corrosion between the first filling metal and the body after the first step, and
the first filling metal and the second filling metal have different ionization tendencies.

16. The method of claim 15, wherein the ionization tendency of the second filling metal is higher than that of the first filling metal, and
the concentration of reactive oxygen species generated in the second step is lower than the concentration of reactive oxygen species generated in the first step.

17. A method of controlling a generation rate of reactive oxygen species using an implant having a groove formed to have different cross-sectional areas and filled with a filling metal having a higher ionization tendency than that of a body, the method comprising:
a first step of generating reactive oxygen species by ionization of the filling metal having a first cross-sectional area; and
a second step of generating reactive oxygen species in a concentration different from a concentration of reactive oxygen species obtained in the first step by ionization of the filling metal having a second cross-sectional area different from the first cross-sectional area after the first step.

18. The method of claim 17, wherein the concentration of reactive oxygen species generated in the second step is lower than the concentration of reactive oxygen species generated in the first step.

19. A method of manufacturing an implant having a controlling generation rate of reactive oxygen species, the method comprising:
preparing a body having a groove;
filling one region inside the groove with a first filling metal; and
filling another region on the first filling metal with a second filling metal,
wherein the second filling metal has an ionization tendency different from an ionization tendency of the first filling metal.

20. The method of claim 19, wherein the second filling metal has a higher ionization tendency than that of the first filling metal.

21. The method of claim 19, wherein the fillings with the first and second filling metals are performed by directly inserting the first and second filling metals into the groove.

22. The method of claim 19, wherein the fillings with the first and second filling metals comprise:
injecting a molten fluid of the first filling metal into the groove and solidifying the molten fluid; and
injecting a molten fluid of the second filling metal onto the first filling metal and solidifying the molten fluid.

23. The method of claim 19, wherein the fillings with the first and second filling metals comprise:
inserting a powder of the first filling powder to the groove and sintering the powder; and
inserting a powder of the second filling metal onto the first filling metal and sintering the powder.

24. The method of claim 19, wherein the fillings with the first and second filling metals comprise:
sequentially inserting powders of the first filling metal and the second filling metal to the groove and sintering the powders.

25. A method of manufacturing an implant having a controlled generation rate of reactive oxygen species, the method comprising:
preparing a body having a groove; and
filling at least one region of the groove with a filling metal,
wherein the groove comprises an upper region having a larger cross-sectional area than a cross-sectional area of a lower region, and
the filling of the groove with the filling metal comprises filling the groove with the filling metal up to a portion of the upper region.

26. The method of claim 25, wherein the filling of the groove with the filling metal is performed by directly inserting the filling metal into the groove.

27. The method of claim 25, wherein the filling of the groove with the filling metal comprises injecting a molten fluid of the filling metal into the groove and solidify the molten fluid.

28. The method of claim 25, wherein the filling of the groove with the filling metal comprises injecting a powder of the filling metal to the groove and sintering the powder.

29. An implant having a controlled generation rate of reactive oxygen species, the implant comprising:
a body formed in a shape corresponding to an implant hole of a fixation plate having a plurality of implant holes formed at intervals through which fixing implants configured to fix a fracture part of a broken bone are inserted, and inserted into a position corresponding to the fracture site of the bone among the implant holes; and
a first filling metal filling a recessed portion recessed from one surface of the body,
wherein the first filling metal has an ionization tendency higher than an ionization tendency of a metal constituting the body.

30. The implant of claim 29, wherein the body is made of one metallic material selected from titanium (Ti), a Ti alloy, stainless steel, and a cobalt-chromium (Co—Cr) alloy.

31. The implant of claim 29, wherein the first filling metal is zinc (Zn), a Zn alloy, magnesium (Mg), or an Mg alloy.

32. The implant of claim 29, wherein a second filling metal having a higher ionization tendency than that of the first filling metal fills the recessed portion on the first filling metal.

33. The implant of claim 32, wherein the first filling metal is zinc (Zn) or a Zn alloy, and
the second filling metal is magnesium (Mg) or a Mg alloy.

34. The implant of claim 32, wherein the first filling metal is iron (Fe) or a Fe alloy, and
the second filling metal is Zn, a Zn alloy, Mg, or a Mg alloy.

35. The implant of claim 29, wherein the recessed portion comprises an upper region having a larger cross-sectional area than a cross-sectional area of a lower region, and the first filling metal fills at least one portion of the upper region having the larger cross-sectional area than that of the lower region.

36. A fracture fixation device comprising:
a fixation plate disposed on at least one portion of a broken bone and having a plurality of implant holes formed at intervals;

a first fixing implant penetrating one of the plurality of implant holes of the fixation plate to be inserted into a first fracture part of the bone to fix the first fracture part;

a second fixing implant penetrating another implant hole of the fixation plate to be inserted into a second fracture part of the bone to fix the second fracture part; and a functional implant engaged into another implant hole of the fixation plate at a position corresponding to a fracture site of the bone, generating reactive oxygen species, and supplying the reactive oxygen species to the fracture site.

37. The fracture fixation device of claim 36, wherein the functional implant does not comprise a threaded portion extending downward from a head portion and inserted into at least one portion of the bone.

* * * * *